United States Patent [19]

Sugarman et al.

[11] Patent Number: 4,858,620
[45] Date of Patent: Aug. 22, 1989

[54] WARNING SYSTEM FOR EXCESSIVE ORTHOPEDIC PRESSURES

[75] Inventors: Edward D. Sugarman, Fayetteville; Nicholas F. D'Antonio; Nicholas J. D'Antonio, both of Liverpool, all of N.Y.

[73] Assignee: Walgen Corporation, Syracuse, N.Y.

[21] Appl. No.: 96,667

[22] Filed: Sep. 15, 1987

Related U.S. Application Data

[63] Continuation-in-part of Ser. No. 834,609, Feb. 28, 1986, abandoned.

[51] Int. Cl.$^4$ .................................................. A61B 5/10
[52] U.S. Cl. .................................... 128/774; 178/694; 73/172
[58] Field of Search ......... 128/694, 774, 748; 73/172, 700, 715, 716, 717, 720, 723, 729

[56] References Cited

U.S. PATENT DOCUMENTS

| | | | |
|---|---|---|---|
| 2,558,805 | 7/1951 | Yaglon | 73/172 |
| 3,978,849 | 9/1976 | Geneen | 128/690 |
| 4,055,078 | 10/1977 | D'Antonio et al. | 73/862.68 |
| 4,122,837 | 10/1978 | Leonard | 128/774 |
| 4,240,288 | 12/1980 | D'Antonio et al. | 73/862.68 |
| 4,286,603 | 9/1981 | Marshall | 128/782 |
| 4,312,361 | 1/1982 | Nicholson et al. | 128/748 |
| 4,502,491 | 3/1985 | Ender et al. | 128/748 |
| 4,554,930 | 11/1985 | Kress | 128/774 |

Primary Examiner—Kyle E. Howell
Assistant Examiner—John C. Hanley
Attorney, Agent, or Firm—Wall and Roehrig

[57] ABSTRACT

A small, inexpensive, but reliable pressure warning system includes a plurality of pressure sensors which are disposed between an orthopedic restraining member and an injured portion of a patient's body, and a processor and alarm unit coupled to the pressure sensor and providing a warning when the pressure reaches a danger level (i.e. 30 mm) in which medical assistance is required. If the pressure goes above a critical value (i.e. 35 mm), another warning is provided that immediate medical attention is needed. The processor and alarm unit can be mounted directly on the patient's cast and are disposable, one-use items.

20 Claims, 4 Drawing Sheets

WARNING SYSTEM FOR EXCESSIVE ORTHOPEDIC PRESSURES

BACKGROUND OF THE INVENTION

This application is a continuation in part of Serial No. 834,609, filed February 28, 1986, abandoned.

The invention relates to medical devices, and is more particularly directed to a device for continuously monitoring the condition of soft tissues that are confined, e.g. in a cast.

Confinement of injured tissue can result in trauma from bleeding and swelling of that or adjacent tissue, and if unchecked can result in permanent injury or death. The reasons for this problem are as discussed below.

The arms and legs are considered to be divided into circumferentially spaced compartments, with each compartment containing muscles and tissues. When the limb is well and uninjured, confinement of the limb does not present any real problems. However, after injury there is potential danger as the pressure within the arm or leg increases due to swelling. The danger is increased by bleeding in the area of the injury after the application of a cast or other rigid dressing, which confines the swollen tissue of the compartments.

In the case of fracture or soft tissue injury, confinement and immobilization creates a substantial risk of increasing vascular and tissue pressure that can result in the closure of vessels and destruction of nerves. Permanent injury to the limb can result. This phenomenon, known as Compartment Syndrome, is one of the most dreaded complications that can face the patient and the physician.

Three interrelated causes are considered as the origin of the Compartment Syndrome. These include: (1) arteriole spasms-deprivation of blood supply as a result of spasms of the small muscles in the arteriole walls; (2) increasing pressure that results in excesses of the critical closing pressure of the veins and arteries, which robs the muscles of blood supply, keeping out needed oxygen and the ability to get rid of byproducts of metabolism, leading to muscular and nerve dysfunction; and (3) arteriole-venous tissue compartment pressure gradient increases, which compromises capillary blood flow and causes muscle tissue death.

An increase in pressure in one compartment causes deprivation of the needed oxygen for the muscle and nerve in adjacent compartments with a resulting functional loss which can be either temporary or permanent depending on the action taken.

After a fracture or other trauma, swelling of the injured tissue begins. When the limb has been placed in a cast, pressure gradients will rise exponentially with time. A rapid increase in pressure requires early detection and relief to avoid catastrophic loss of the patient's limb. Relief is accomplished by the removal or substantial loosening of the cast or rigid dressing, once a damage-level pressure condition is detected.

Normal tissue pressure is considered zero millimeters (mm) of mercury. Elevated pressures above about 50 mm of mercury can result in permanent damage to muscle and nerve tissue. The zone of temporary damage is between 30 and 40 mm of mercury. Pressure reduction by loosening or removal of the cast is required to save the arm or leg, but must be done soon enough, i.e. before there is permanent tissue loss. On occasion, the tissues will swell at a rate requiring surgical opening of the fascia that enclose the compartment. Therefore, the danger must be recognized early on before permanent damage is done, and action to remove the cast pressure must be fast and complete.

To prevent catastrophic loss, the limb must be constantly monitored for pressure and for rapid changes in pressure beneath a cast or dressing regardless of where the patient might be situated.

Several methods of pressure measurements have been developed with varying degrees of success but all have shortcomings. Some require insertion of a sensor under the skin. Such methods can increase complications by infection and seriously impede the patient's mobility. The units for these methods are typically large and expensive, selling for between $2,500–$3,500. Because these require a 110 V AC electrical source, they are not suited for portability or mounting directly on a cast and generally require the patient be hospitalized.

As noted, Compartment Syndrome, as the name implies, results from the interaction of different events that are occurring simultaneously beneath an orthopedic restraining member or cast. The use of a single pressure sensing element cannot monitor all these occurrences at one time and provide accurate data upon which an early decision can be made concerning loosening or removal of the restraining member. What is required under these conditions is simultaneous pressure related information from each compartment that can be processed to provide extremely accurate data upon which decisions relating to the dispostion of injury can be based.

OBJECTS AND SUMMARY OF THE INVENTION

It is an object of this invention to provide a tissue presssure monitoring device that avoids the drawbacks of prior art devices.

It is another object of this invention to provide a pressure monitoring device which is noninvasive, reliable, low cost and disposable, and which can be installed as a part of a cast or confining structure to recognize when the pressure beneath the cast approaches dangerous limits.

It is a more specific object of the present invention to provide a self-contained pressure monitoring unit that employs visual and audible alarms to alert medical or lay persons when the pressure or the rate of change of pressure beneath a cast exceeds given limits.

A still further object of the present invention is to provide a device for monitoring the rate of change in pressure beneath a cast or the like.

The warning device of this invention is preferably a two part entity comprising (a) a plurality of sensor elements and (b) a microprocessor based power and warning unit having indicator lights and a buzzer, sounder, or other audible or visible alarm for producing a discernable warning signal when excessive pressure is detected beneath a cast or restraining member. The sensor elements are circumferentially placed on the skin of the injured limb over each compartment and the cast or dressing is formed over the sensor elements. The latter are connected to the power and control unit by waterproof cable.

While system operation is described and illustrated for specific values of pressure and pressure ranges, it is understood that simple design changes will allow for different ranges of input signals and methods of output warning. For example, if pressure builds to the 30–35 mm range, a yellow warning light and/or LED comes on. As the pressure increases beyond 35 mm, a red lamp or LED is turned on, and/or an audible alarm sounds. This gives a clear warning to the patient or anyone in attendance so that the patient can reach a hospital or the physician's office in time for appropriate relief. In addition, the red lamp or LED lights and an audible alarm could also be made to sound if the sensor or transducer network are improperly adjusted to a value less than zero.

The power and warning unit is self-contained, battery powered, and low cost and is considered disposable. The power and warning unit include a microprocessor unit to control the warning lights and audible alarm based on the proper adjustment of the transducer and the pressures measured by the pressure sensor units, A digital readout of the pressure sensed is also provided.

The device, which can be affixed on a cast or installed as part of the cast, continuously monitors the pressure of the limb compartments, and warns of any significant pressure buildup, especially during the first thirty-six to forty-eight hours after the injury, that being the period when compartment syndrome might be expected. The patient's condition can be monitored by the patient himself, or by his family. This reduces the need for hospital confinement, enabling the injured patient to return home sooner.

The above and many other objects, features, and advantages of this invention will be more fully appreciated from the ensuing description of a preferred embodiment, which should be read in connection with the accompanying drawing.

DETAILED DESCRIPTION OF THE PREFERRED EMBODIMENTS

Figures 1, 4:
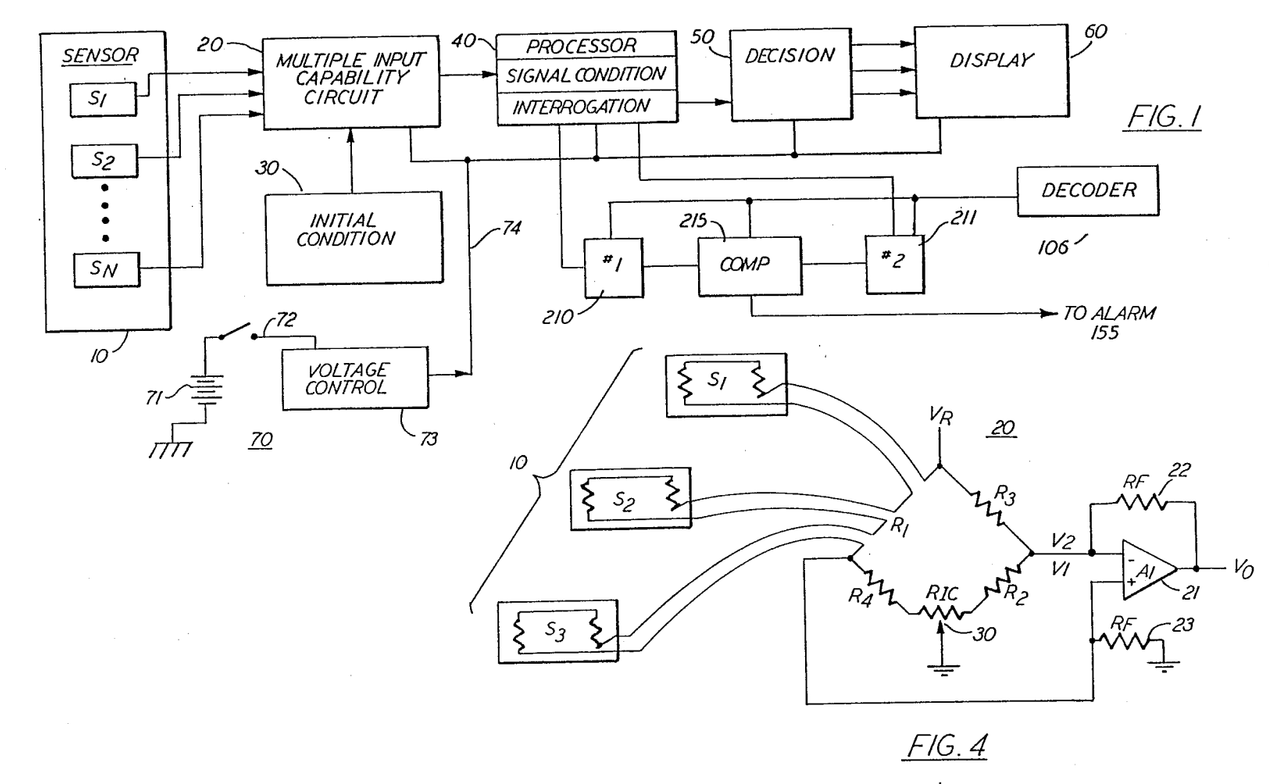
FIG. 1 is a system block diagram of the orthopedic pressure warning system according to one embodiment of this invention.
FIG. 4 is a variant of the analog bridge and amplified circuit of FIG. 2.

With reference to the drawing, FIG. 1 diagrams, as elements of the circuit, seven basic functions carried out within the system of preferred embodiments of this invention. Here, design guidelines are dictated by the need for small size, mobility, low-power battery operation, environmental consideration, and low cost. Each of the seven functions is intended to be relatively simple, so that the structure avoids a grossly complicated design. In fact, a key objective of this system is simplicity.

Figures 2, 7:
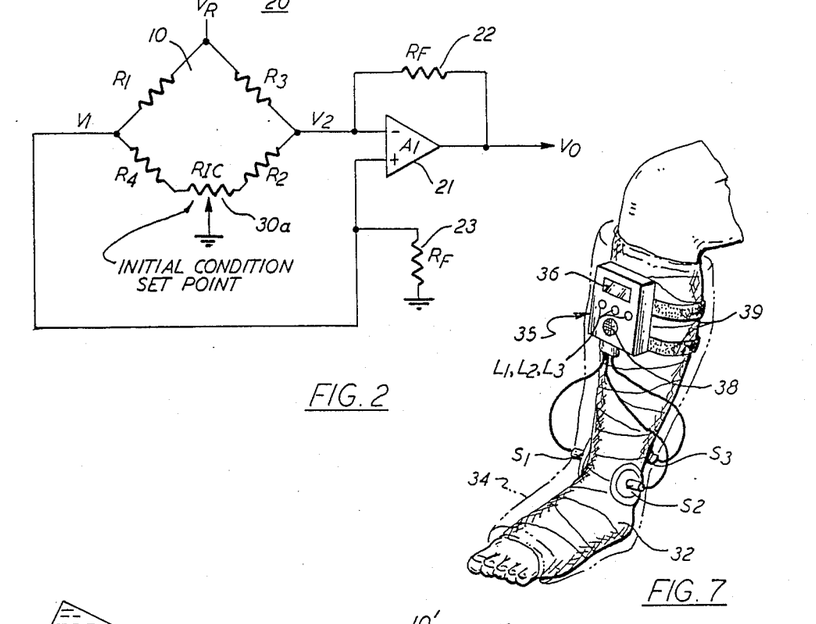
FIG. 2 is a simplified diagram of an analog bridge and amplifier circuit which can be employed as a component of embodiments of this invention.
FIG. 7 is a partial perspective view showing the present invention mounted upon a patient's limb.

A sensor arrangement 10 includes a number of separate sensor elements S1, S2 .... Sn, hereinafter defined as the electrical elements reacting to the source pressure. These sensors receive the applied pressure by way of a pad which is disposed over a compartment beneath a cast or other restraining member, such as an arm or leg of a fracture victim as illustrated in FIG. 7. These sensor elements S1, S2, ... Sn can employ fluid transmission or direct electrical sensing of the applied pressure to realize the required pressure dependent variation. It is important that the sensor elements S1, S2, ... Sn, have the characteristics of linearity and repeatability, at least within the operative range, which, here is about zero to about 50 millimeters of mercury, i.e., about zero to about one psi. The sensor elements S1, S2, ... Sn should also have range and sensitivities selected to avoid excessive response to extraneous signals and noise.

The sensor elements of the sensor arrangement 10 are coupled to a circuit 20. This circuit 20 converts any parameter change in the sensor elements S1, S2, ... Sn into a useable electrical signal for subsequent processing. In the preferred embodiments discussed herebelow, the circuit 20 is of analog type; however, a digital or frequency technique could be employed instead, with comparable effectiveness. The particular sensor elements S1, S2, ... Sn used would dictate the type of circuit 20 that is used with them. As with the sensor arrangement 10, the circuit 20 must have the characteristics of linearity and sensitivity over the appropriate range, and its output signal characteristics will affect the remaining stages of the system.

An initial condition set arrangement 30 is employed for zeroing the system to prevent the dangerous situation where the circuit 20 is inadvertently adjusted to a value that is less than zero, and also to provide an initial non-zero set point, if that is desired or needed. In other words, the arrangement 30 is employed for avoiding the dangerous less than zero adjustment and/or for selectively adjusting the output level of the circuit 20 for given input signals from the sensor arrangement 10. The initial condition set arrangement 30 is adjusted by the attending physician, as dictated by his or her experience with the type of problem the patient is suffering, and is adjusted when the patient's condition suggests that a significant internal pressure may have already developed. The form that the initial condition set arrangement 30 takes depends on the type of transducer and circuit 20 that are employed.

A processor circuit 40 receives the output signal of the circuit 20, and conditions the signal for a decision logic circuit 50 so that the latter can determine if a less than zero setting has been avoided and if a significant pressure change event has happened since the previous measurement. The processor 40 has two basic sections, a signal condition section that transforms the output signal from the circuit 20 to a form compatible with the second or signal interrogation section, the latter taking measurements at regular intervals to determine if the circuit 20 output signal has changed significantly.

The decision logic 50 selectively interrogates the processor circuit 40, and activates appropriate portions of display and/or warning networks 60 which follow the decision logic 50. The display and warning networks 60 provide an indication to the outside world about the critical below-zero adjustment, or, in actual use, the condition of the patient. In the preferred embodiment, two means of display are employed: an LCD numerical display presents the actual pressure as detected by the sensor S1, S2, ... Sn, and another visual display consisting of green, yellow, and red LEDs presents an easily distinguishable visible warning, if a critical situation occurs. This network 60 can further include an audible warning or sounder which alarms when a below-zero or critical sensor level is reached.

A self-contained power supply 70 includes a built-in battery 71 which serves as a voltage and current source for the remaining elements listed above. This battery 71 is selected to be of sufficient size and voltage for powering the system load for an acceptable period of time, i.e., for at least the first 48 hours after a cast is placed on a patient. With the use of high impedance sensors, low power CMOS electronic functions and well defined time spacial interrogations by processor 40, useful life well in excess of ten weeks has been demonstrated. Decay characteristics of the battery 71 are such that it maintains a more-or-less level voltage characteristic over the period of use. The battery is coupled by a one-way switch 72 through a voltage control or regulation circuit 73 and a power bus 74 to the various elements 20, 40, 50 and 60. The one-way switch 72, which is capable of being turned on only, permits the physician to turn the system on when the system is installed in a housing on the patient's cast, but prevents the system from being switched off inadvertently by the patient. By the time the battery 71 wears out, the patient no longer needs the device.

A number of commercially available sensors and circuits can be used in the sensor arrangement 10 and the circuit 20 of the system of this invention. The pressure sensors and corresponding circuitry are required to be small, low cost, and reasonably rugged for realization of a practical and disposable device. A suitable arrangement is described in U.S. Patent Nos. 4,055,078 and 4,240,288 the contents of which are incorporated herein by reference. Both of these U.S. Patents disclose a low-cost, low power consumption system arranged in a conventional resistive bridge circuit so that an output voltage of the bridge circuit is linearly related to the applied force or pressure on the sensor elements coupled to one or more legs of the bridge circuit. A vehicle for explaining the operation is shown in FIG. 2, where R1, R2, R3, and R4 are arranged in a resistive bridge, with an applied constant voltage $V_R$ being applied to the juncture of legs R1, and R3 and with a variable resistor $R_{IC}$ bridging between the R2 and R4 legs and having a slider coupled to ground. This resistor $R_{IC}$ serves as an initial condition setting circuit 30a and is adjusted to set the initial condition set point. A pair of voltages V1 and V2 are taken from the junctures of the elements R1 and R4 and of the elements R3 and R2 respectively. These voltages are applied to a circuit, which includes a differential amplifier 21 and a pair of resistors 22, 23, both of value $R_F$. The non-inverting input of the operational amplifier 21 is coupled through the resistor 23 to ground, and receives the voltage V1. The inverting input receives the voltage V2, and is coupled to the output of the operational amplifier 21 through the feedback resistor 22.

Sensor elements S1–Sn can couple with, or directly replace, one or more legs of the bridge network shown in FIG. 2, and are available for local or distributed mounting, similar to the arrangement with a conventional strain gauge bridge. The sensor elements S1–Sn of this arrangement are considerably lower cost than strain gauge elements, and are much easier to mount. Further, the resistance values of the elements S1–Sn can easily be in the range of 50 Kilohms, or above, so that the sensor load to the battery 71 is in the microampere current range. In contrast to this, most strain gauges have a maximum resistance of 1 Kilohm, and could not be used with a small battery for any sustained period of time.

In terms of a general explanation for the operation of the FIG. 2 arrangement, if R1 and R2 are configured as the pressure sensitive legs of the bridge, when pressure is applied, their resistance decreases. Consequently, the voltage V2 drops and the voltage V1 rises. The amplifier 21 will amplify the difference voltage and provides an output V0 according to the formula $V0 = K(V1 - V2)$. The value $R_F$ of the resistor 22 is selected in conjunction with the static resistance values of the legs R1–R4, so as to provide a maximum output voltage from the amplifier 21 that is appropriate to the expected maximum pressure applied to the sensor elements, in this case, the R1, R2 legs of the bridge. Resistor 23 will normally have the same value as feedback resistor 22 in order to provide a balanced impedance for the two amplifier inputs.

Figure 3:
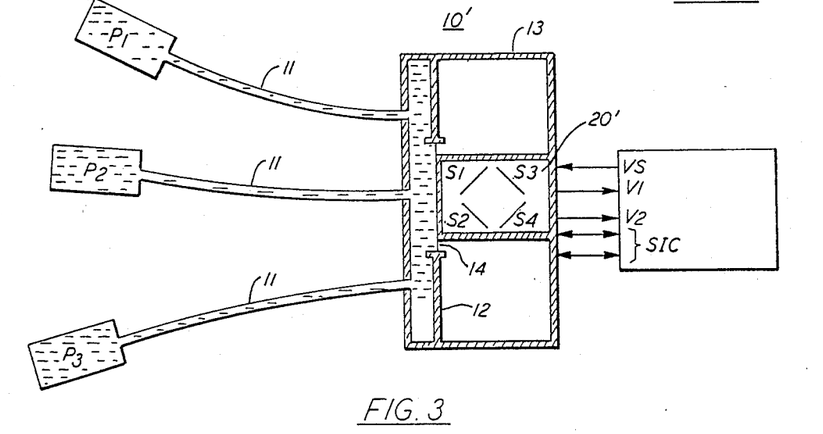
FIG. 3 is a diagram of a fluid transducer arrangement which can be employed as a component of embodiments of this invention.

Another transducer arrangement is illustrated in FIG. 3. In this embodiment, the sensors receive the applied pressure by way of the fluid-filled pads P1, P2, P3 coupled by connecting tubes 11 to a fluid chamber 12 within a central collection housing 13. Pressure transmitted from the pads P1, P2, P3 to the chamber 12 presses against a receiver plate or diaphragm 14, and the latter presses against a sensor module 20' also contained within the housing 13. Pressure applied to the remote pads P1, P2, P3 and transmitted through the connecting tubes 11 to sensor module 20' causes the latter to output the voltage corresponding to the sensed pressure. Sensor module 20' can be considered as having active legs S1–S4 within it. As the receiver plate 14 receives the pressure from the pads P1, P2, P3 the legs are actuated, and as described in U.S. Patent Nos. 4,055,078 and 4,240,288 and hereinbelow, the impedance of the S1 and S2 legs decreases, while the impedance of the S3 and S4 legs increases. With four active legs, this arrangement has greater sensitivity by a factor of four than transducer bridges with only a single active leg. Sensor module 20', as shown in FIG. 3, is illustrated in detail in FIGS. 8 and 9. Sensor module 20' comprises sensors S1 S4. Sensors S1–S4 are connected together to form a balanced bridge circuit as shown in FIG. 2. A power source, differential bridge amplifier, and balancing resistor would normally be connected to sensors S1–S4 when the sensor module is operating. Module 20' further includes a base plate 302, a force transmitting member 304, a clamping member 306, and a pre-load screw 308. Base plate 302 has appropriate grooves 310 in which sensors S1–S4 can be nested, and force transmitting member 304 and clamping member 306 have corresponding grooves 312 and 314, respectively, for receiving the respective opposite portions of the sensors to clamp the latter elements in place as shown. Grooves 310–314 are dimensioned to be less than the diameters of sensors S1–S4, so that gaps 316 and 318 exist between member 302, and members 304 and 306, when sensors S1–S4 are in place.

Figure 8:
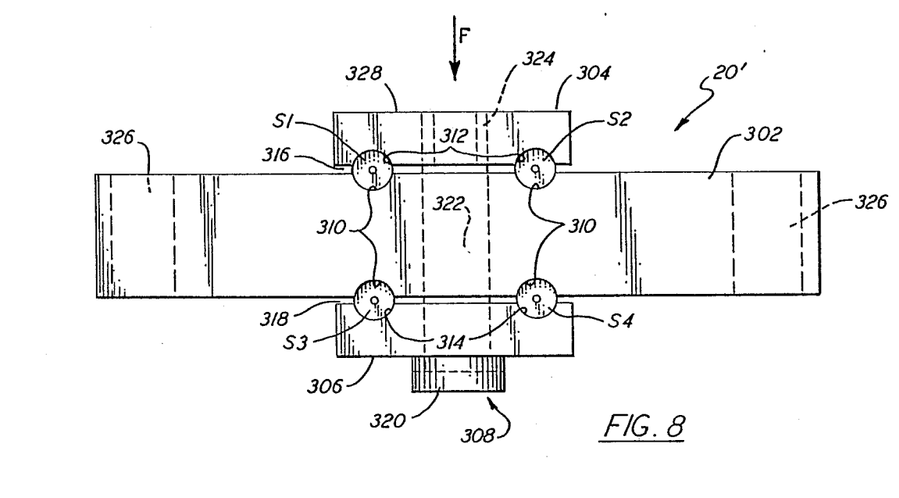
FIG. 8 is an elevation view of a sensor module employed in one embodiment of the claimed invention.
Figure 9:
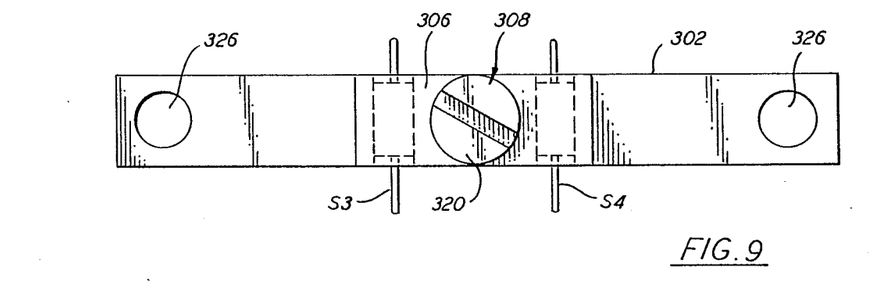
FIG. 9 is a bottom plan view of the sensor module employed in one embodiment of the claimed invention.

Pre-load screw 308 has a slotted head 320, and a shaft 322 which extends through coaxial central bores extending through each of members 302–306. Shaft 322 terminates in a threaded portion 324, which threads are engaged by corresponding threads in force applying member 304. Base member 302 further includes mounting holes 326, through which appropriate fasteners can extend for securing module 20' to some apparatus in which the module is to be incorporated. Preferably, sensors S1-S4 are selected in their sequential order of manufacture from a single production run to achieve the equality of conductive transfer function along with the thermal and physical characteristics referred to earlier.

In operation, the component parts of module 20' are assembled as shown in FIGS. 8 and 9. Pre-load screw is tightened to draw members 304 and 306 against sensors S1-S4 by an amount sufficient to pre-stress these elements sufficiently to exceed any expected unloading which will occur when force is applied to the sensors and preferably to alter the force response characteristics of the sensors to effectively eliminate nonlinear operation. In a normal production situation, the amount by which screw 308 would have to be tightened would be predetermined, so that this operation could be accomplished using automated tightening equipment.

Module 20' is situated in its operating environment so that the external force to be measured or monitored is applied to surface 328 of force transmitting member 304. In FIG. 3, diaphragm 14 and force transmitting member 304 are juxtaposed such that the pressure transmitted to chamber 12 causes diaphram 14 to exert a force F against force transmitting member 304.

Force F is transmitted to sensors S1 and S2 to reduce their respective impedances; and force F is further transmitted to clamping member 306 to relieve the pre-stress on sensors S3 and S4. Force F thus has the total effect of simultaneously reducing the impedance in sensor S1 while increasing the impedance in element S4 by an amount equal to the decrease in sensor S1, and further reducing the resistance in sensor S2 while effecting a corresponding increase in the impedance in element S3. The net effect of the application of force F is to enhance the value of $(V_1-V_2)$ by applying or relieving the force to all of the sensors in the bridge, which was the desired result.

In applications calling for monitoring forces applied at diverse locations (see, e.g. FIG. 4), the sensors forming the bridge circuit might be disposed in independent force transmitting apparatuses, although this could limit the simultaneous application of stress to all of the sensors to achieve the output enhancement described herein.

Another arrangement for detecting a remote pressure is shown in FIG. 4. In this embodiment, three electrical pressure sensors S1, S2, and S3 are connected in series as one sensor leg R1 of a bridge circuit and therein are an integral part of the bridge structure. As pressure is applied to any of the pads, the impedance in the R1 leg of the bridge (i.e., S1-S3) will decrease while the impedance of the remaining legs, R2, R3 and R4 remain constant. The impedance change in the R1 leg causes a corresponding increase in the voltage output V0 of the amplifier 21, with the output voltage V0 indicating a change in the overall pressure sensed. The impedance values of the sensors S1, S2 and S3 are algebraically summed together in the R1 leg.

In applications for sensing the pressure beneath the surface of an orthopedic cast, a slender profile for the sensor pads P1, P2, and P3 is very desirable. The slender profile is easy to realize with the fluid-filled pad of FIG. 3 and also with the electrical sensor pad of FIG. 4. While true that the single active format of FIG. 4 results in a lower overall transducer sensitivity, the availability of the R2, R3 and R4 legs will provide means for a simple, low cost method of temperature compensation described below.

A distinct advantage of the arrangement of FIG. 4 is that all three sensor pads can be coupled to the system housing either at the time of assembly or later. This permits the system housing to be replaced in the case of battery depletion or malfunction without having to remove the original cast and pad arrangement.

As noted above, the arrangement of FIG. 4 also achieves a low cost, simple, but effective means for achieving temperature stability. This operates by providing a fourth "pad" carrying the remaining legs R2, R3, and R4 of the bridge. This fourth pad is also disposed beneath the cast or restraining member, preferably in the vicinity of the housing for the system. This technique achieves temperature stability by placing all four legs of the bridge at the same temperature as the patient's body. It should be further noted that the electrical system described with reference to FIG. 4 is also insensitive to changes in atmosphere pressure produced by change in altitude or atmospheric pressure. Accordingly, the device will operate effectively without adjustment whether the patient is at a single location or being transported in an evacuation aircraft or the like.

Figures 5, 6A, 6B, 6C, 6D:
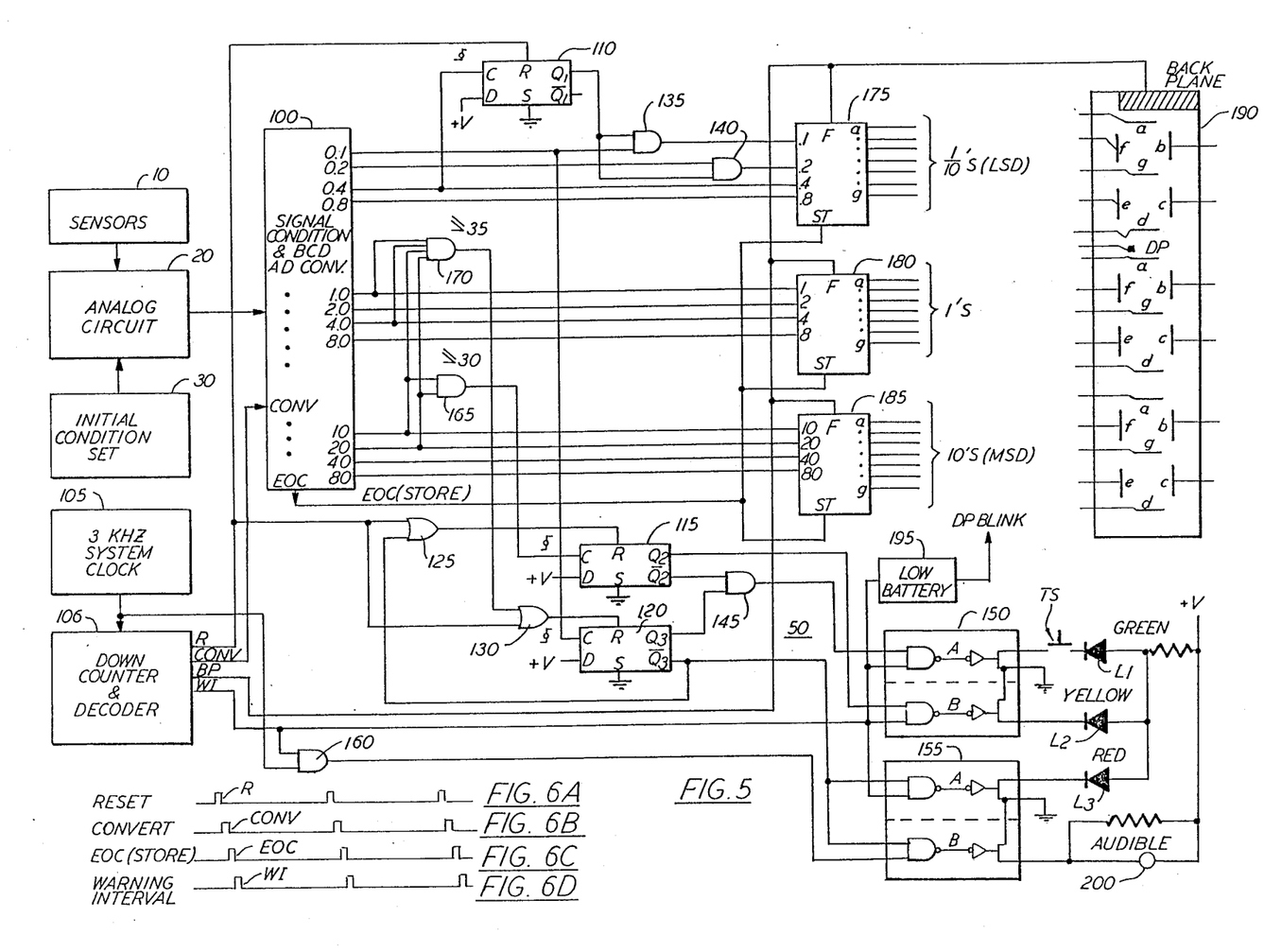
FIG. 5 is a system schematic diagram of a control program and alarm circuit of an embodiment of this invention.
FIGS. 6A, 6B, 6C, and 6D are diagrams of timing signals employed in the circuit of FIG. 5.

FIG. 5 is a circuit arrangement of the system of a preferred embodiment, showing details of the processor circuit 40, the decision logic circuit 50, and the display and alarm network 60. Initially, circuit 20 output voltage V0 is applied to an input of a signal condition and binary coded decimal (BCD) analog to digital converter 100, having tens, units, and tenths outputs. This circuit 100 can also include the amplifier 21. This converter circuit 100 is commercially available from a number of reliable manufacturers, one such circuit being the Datel Corporation Model No. ADV-EK12D, which is a three-digit BCD device, supplied in compact, monolithic form, and is suited for use in a portable, lightweight device, such as the device of the present invention. However, functional design of the FIG. 5 processor requires an A/D Conversion with a real time digital up-count for proper system operation, therefore, circuit 100 utilizes an alternative approach as disclosed in U.S. Patent No. 4,387,307. The latter approach is capable of a low cost, low power device which is readily included as part of a custom or semi-custom CMOS integrated circuit as presently anticipated for a high volume, low cost, low power, disposable device of the present disclosure. The only difference between the requirements of the present application and Patent No. 4,387,307 is that the adaptive capability of the latter is unnecessary and the conversion up-counter is a three digit BCD code rather than the Binary code of the earlier disclosure.

A system clock 105 operates at a frequency that is compatible with the operating range of a low power piezo electric sounder, as mentioned later. As all other functions operate at a significantly lower frequency, a down counter/decoder 106 follows the system clock 105, and provides in sequential order, the origin of five digital signals beginning with (but not shown in FIG. 6) a 104 Hz back plane frequency for LCD operation and further including a reset timing pulse R (FIG. 6A), a convert timing pulse CONV (FIG. 6B), an end of convert pulse EOC (FIG. 6C), generated by the ADC at the end of the convert interval and a warning interval pulse WI (FIG. 6D). The timing signals are presented in the order shown, that is, following the back plane frequency, the reset pulse R, convert pulse CONV, end of convert pulse EOC, and the warning interval pulse WI.

At the onset of a measurement interval, the reset pulse R is generated, and this resets three flip-flops, 110, 115, and 120. The latter are coupled to the down counter 106 through OR gates 125 and 130 respectively. As a result of the reset pulse R, the output level Q1 of the flip-flop 110 is made low, and this provides a low output to AND gates 135 and 140. The outputs Q2 and Q3 of the flip-flops 115 and 120 are both rendered low, and their inverted outputs Q2 and Q3 are high. The latter inverted output Q3 is applied to an input of the OR gate 125. The inverted output Q2 of the flip-flop 115 and the uninverted output Q3 of the flip-flop 120 are both applied to inputs of an AND gate 145. Drive logic circuits 150 and 155 each have A and B portions, the A and B portions of the circuit 150 having inputs respectively coupled to the output of the AND gate 145, and to the Q2 output of the flip-flop 115 while the A and B portions of the circuit 155 have inputs coupled to the inverted output Q3 of the flip-flop 120. The circuits 150 and 155 also have inputs connected to receive the warning interval pulses WI of FIG. 6D. The warning interval pulses WI and the clock pulses from the system clock 105 are supplied through an AND gate 160 to an input of the B portion of circuit 155. Also shown in this circuit is an AND gate 165, having inputs coupled to the "10" and "20" outputs of the converter circuit 100, and another AND gate 170 having inputs coupled to the "10", "20", "4.0" and "1.0" outputs thereof. The AND gate 165, has an output coupled to a clock input C of the flip-flop 115, while the AND gate 170 has its output coupled through the OR gate 130 to the reset terminal R of the flip-flop 120. The clock terminal C of the flip-flop 120 is coupled to the "0.1" output of the converter circuit 100.

Three respective drive circuits 175, 180, and 185 have inputs coupled to the tenths outputs, units outputs, and tens outputs, respectively, of the converter circuit 100. However, the AND gates 135 and 140 intervene in advance of the "0.1" and "0.2" inputs of the drive circuit 175. The circuits 175, 180, and 185 have outputs for driving respective digits of a liquid crystal display 190. The back plane frequency of down counter 106 is supplied to terminals F of the circuits 175, 180, and 185, and to a back plane input of the display 190.

A low battery sense circuit 195 has an input coupled to receive the warning interval pulses WI, and an output coupled to the decimal point segment of liquid crystal display 190 so that the decimal point will blink intermittently if the level on the battery 71 drops below a predetermined threshold.

Following the A and B portions of the circuits 150 and 155 are a green LED L1, a yellow LED L2, a red LED L3, and an audible alarm 200. A normally-open test switch TS is interposed in advance of the green LED L1. At the onset of the measurement interval, following the reset pulse R, the Q1 output of the flip-flop 110 is made low, and the AND gates 135 and 140 become disabled to blank out the display of digits "0.1", "0.2" and "0.3" on the liquid crystal display 190. This means that the tenths digit will not appear until the converter circuit 100 produces a value of 0.4 or above. At 0.4, the positive-going edge of the "0.4" digit from the progressive up-count output of the converter circuit 100 will set the flip-flop 110; this causes its output Q1 to become high, thus enabling the AND gates 135 and 140, so that all digits, including the "0.1", "0.2", and "0.3" will then appear when called on by converter circuit 100. The "blanking" by the gates 135 and 140 of the early digits is intended to avoid confusion when a set point of zero is used. Thus, as the device is being adjusted in the vicinity of zero, according to the patient's condition, the gates 135 and 140 permit the device to be set at one or two tenths beyond zero without having the digits on the display 190 intermittently jump in and out of the warning zone for the inadvertent below-zero adjustment of circuit 20. This prevents unnecessary annoyance to the patient, with negligible error in the actual reading.

If an improperly adjusted circuit 20 causes amplifier 21 of circuit 20 to imply a pressure signal of less than zero, the 0.1 transition of converter 100 will not occur. This causes inverted output Q3 of the reset flip-flop 120 to remain high to therein enable the A and B portions of drive circuit 155. With the latter enabled, the warning interval pulse WI will cause the red LED L3 to blink while at the same time audible alarm 200 is activated with the 3 KHZ drive signal through AND gate 160. If, on the other hand, the amplifier 21 of the circuit 20 provides the voltage $V_0$ at a level indicating a pressure greater than zero, the "0.1" transition will occur and flip-flop 120 is clocked. This makes the normally low Q3 output high, while the normally high inverted Q3 output goes low. The lfip-flop 115, which has been reset by the pulse R, keeps its inverted output Q2 high. These outputs are both provided to the AND gate 145 as high signals, and so the A portion of the driver circuit 150 is enabled. Then, when the warning interval WI pulse occurs, the green LED L1 is activated, and provides an all-clear signal when the test switch TS is depressed. In order to avoid unnecessary current consumption, the green LED L1 will not light unless the test switch TS is pressed.

If the pressure level continues to increase until the converter circuit 100 produces a BCD value of "30" or more, high levels on the "10" and "20" digit will enable the AND gate 165, and the upward transition of this gate 165 will clock the flip-flop 115. The output Q2 thereof then is made high to enable the B portion of the power drive 150, while, at the same time the inverted output Q2 of the flip-flop 115 is made low to disable the AND gate 145. Then, the A-portion of the driver 150 and the green LED L1 are deenergized. When the next warning interval pulse WI occurs the yellow LED L2 is energized and it lights to warn the patient that medical attention is required as soon as possible.

If the pressure value continues to increase further, and reaches a value of "35" or more, high levels on the "10", "20", "4.0" and "1.9" digits will enable the AND gate 170. A high output on the gate 170 will reset the flip-flop 120. At that time, the output Q3 of the flip-flop 120 becomes low, and its inverted output Q3 goes high. This results in energization of both the A and B portions of the power driver 155. As explained earlier, this causes both the red LED L3 and the audible sounder 200 to be energized during the warning interval pulse to alert the patient, and anyone else in attendance, that a crisis situation has occurred, and immediate medical attention is imperative in order to avoid serious injury and possible loss of limb. Again, with Q3 inverted output high and AND gate 160 enabled by warning interval WI, the 3 KHz clock signal therein appearing at one input of the B portion of the drive circuit 155 will cause audible sounder 200 to be energized in conjunction with the red LED L3. These clock pulses are strong and highly audible. When the binary coded decimal conversion of the output voltage $V_0$ to digital form is completed, the circuit 100 produces an end-of-convert pulse EOC which is fed to store terminal inputs ST of the drivers 175, 180 and 185. The resulting digital word presented from the tenths, units, and tens bits of the converter circuit 100 are then stored in these driver circuits 175, 180 and 185. The back plane frequency BP continues to energize the liquid crystal display 190, and drives the display 190 with the appropriate numerical value for pressure as supplied by the drive circuits 175, 180, and 185. The low battery alert 195 acts to supply an in-phase/out-of-phase signal so that the decimal point of display 190 will blink. This warns the user that the battery 71 will not be expected to last more than about another 24 hours.

Preferably, in this embodiment the circuit 100, 110, 115, 120, 175, 180, 185 and other elements of this arrangement are of the CMOS type, which have the features of ruggedness and low power consumption and a wide range of operational voltages to choose from.

The sensor elements of the sensor arrangement 10 can be of any convenient type which are reliable and reasonably accurate within the range of about 0 to about 50 millimeters of mercury, and especially in or near the warning zones of 30 to 35 millimeters and in the danger zone of 35 millimeters and above.

As illustrated in FIG. 1, the rate of change in pressure beneath the cast can be monitored and a warning signal generated when this rate of change moves into a predetermined critical range. In some cases the rate of change in pressure might be more indicative of the onset of a potentially dangerous condition than the actual pressure sensed. If the rate rises rapidly, the time to take preventative measures may be relatively short.

The change in rate is monitored by using a pair of memories 210 and 211 that are adapted to store pressure information from the BCD converter 100 at different intervals of time. A first reading is latched into memory 210 at a given time and after an interval, in this case after a one minute delay, a second reading is latched into the second memory 211. The two latched readings are then compared within a comparator circuit 215. In the event the spread between the two readings exceeds a preset condition, the comparator sends an activating signal to alarm circuit 155 (FIG. 5) whereupon audible alarm 200 is triggered and the red LED (L3) is turned on. The memory and comparator circuits are controlled by the system down counter and decoder circuit 106 (FIG. 5).

Referring now to FIG. 7, there is shown a cast 34 surrounding the lower part of a patient's leg. In this case the leg injury is in a region that contains three separate muscle structure compartments. These compartments are easily identified by an attending physician. A pressure sensor is placed over each compartment in the injury region and held in place by the gauze 32. The sensors S1, S2 and S3 are enclosed inside the cast and are connected to an exterior housing generally depicted at 35 by appropriate wire leads. The housing contains the above noted signal processing circuits and an independent power supply for powering the circuits. A digital display window 36 is mounted in front of the housing and provides the patient or an attendant with a numerical readout of the pressure sensed beneath the cast.

A small speaker 38 is also mounted in the face of the housing which, explained above, produces a loud audible signal when the sensed pressure reaches a predetermined critical level or the rate of change in pressure increases at a rapid rate.

Three small color coded lamps L1, L2 and L3 are also mounted in the face of the housing. The first lamp L1 emits green light and is activated when the switch TS (FIG. 5) is depressed thus indicating the system is operating and the pressure sensed is below the predetermined danger level. Lamp L2 emits yellow light and comes on automatically when the danger level is reached or exceeded. This tells the patient he should seek medical help within a reasonable period of time. Lastly lamp L3 emits a red light and informs the patient that he must receive immediate medical aid.

The housing is provided with a Velcro strap 39 that enables it to be conveniently attached to a cast or the patient's limb. The housing and enclosed circuitry is relatively light and small enough so that it can be easily supported upon the limb without being a hazard to the patient.

While this invention has been illustrated with reference to preferred emobidments, it should be understood that the invention is not limited to those precise embodiments, and that many modifications and variations thereof could be carried out by those skilled in the art without departure from the scope and spirit of this invention, as defined in the appended claims.

What is claimed is:

1. An apparatus for monitoring pressure beneath an orthopedic restraining member that has been applied to a person's body, said apparatus comprising:
   sensing means for sensing a pressure level at a plurality of compartments beneath a restraining member, said sensing means includes a plurality of electrical pressure sensors, whereby at least one of said sensors can be situated at each of the compartments,
   means, coupled to the plurality of electrical pressure sensors of said sensing means, for generating an electrical output signal that is proportional to the algebraic sum of said pressure levels sensed at a plurality of compartments, and
   warning means, coupled to said generating means and responsive to the output signal, for warning when said output signal reaches a predetermined danger level.

2. The apparatus of claim 1 wherein said warning means includes a display, responsive to said output signal, for providing a numerical indication of said output signal.

3. The apparatus of claim 1 wherein said generating means further comprises adjusting means for adjusting said output signal to a predetermined initial value.

4. The apparatus of claim 3 that includes means for activating said warning means when the value of said electrical output signal is less than zero.

5. The apparatus of claim 1 wherein said warning means includes an audible alarm that provides an audible signal when said electrical output signal reaches a predetermined value.

6. The apparatus of claim 1 wherein said warning means includes a first light indicator that is actuated when the value of the electrical output signal is within a first range of values, a second light indicator that is actuated when the value of the electrical output signal is within a second range of values, and a third light indicator that is actuated when the value of the electrical output signal is within a third range of values.

7. The apparatus of claim 1 that further includes means, coupled to said generating means, for measuring the value of said electrical output signal at predetermined time intervals to produce a plurality of value measurements, means for storing the value measurements, means, coupled to said measurement means and said storage means, for latching said value measurements into said storage means, means coupled to said storage means, for comparing one of said value measurements with another of said value measurements, and means, connected to said comparing means, for activating an alarm if the difference between the compared value measurements exceeds a given value.

8. The apparatus of claim 1 that further includes a self-contained power supply comprising a battery having an electrical potential, and switch means, connected to said battery and said generating means, for closing an electrical circuit that includes said battery and said generating means.

9. An apparatus as recited in claim 8, further comprising a housing of small dimension relative to a restraining member, said housing being configured to mount on the restraining member and containing said generating means, said warning means, said self-contained power supply, and said switch means.

10. An apparatus as recited in claim 1, further comprising means, coupled to said generating means, for determining a rate of change in pressure level beneath a retraining member; and alarm means, coupled to said determining means, for providing a patient sensible warning as soon as the rate of change in pressure level exceeds a predetermined value.

11. An apparatus for detecting a pressure level beneath an orthopedic restraining member that has been applied to a person's body, said apparatus comprising,
non-invasive pressure sensor means, disposed externally on a portion of a body encircled by a restraining member, for providing pressure signals representing the pressure sustained by said portion of the body at a plurality of compartments beneath the orthopedic restraining member, said signals together indicating attempted changes in volume of the affected portion of the body encircled by the restraining member, said sensing means including a plurality of pressure sensitive fluid-filled pads, whereby at least one of said pads can be situated at each of the compartments;
processor means, coupled to the plurality of fluid-filled pads of said pressure sensor means, for processing said pressure signals to provide at least one output signal having a value that substantially corresponds to the combination of the pressure signals; and
warning means, coupled to said processor means and responsive to the output signal, for warning when said output signal reaches a predetermined danger level.

12. An apparatus as recited in claim 11, further comprising means, coupled to said processor means, for determining a rate of change in pressure level beneath a restraining member.

13. An apparatus as recited in claim 12, further comprising display means coupled to said processor means for providing a numerical indication of the instantaneous pressure level beneath a restraining member.

14. A method of monitoring pressure beneath an orthopedic restraining member that has been applied to a person's body, said method includes the steps of
placing a plurality of pressure sensors at a plurality of compartments beneath an orthopedic restraining member,
sensing a pressure level at a plurality of compartments beneath an orthopedic restraining member,
generating an electrical output signal having a value that substantially corresponds to the combination of the pressure levels sensed, and providing a warning signal in response to a predetermined warning value of said electrical output signal.

15. The method of claim 14 that includes the step of providing a display indicative of the electrical output signal value.

16. The method of claim 14 that includes the step of adjusting said output signal to a predetermined initial value.

17. The method of claim 14 that further includes the step of sounding an audible alarm when said electrical output signal reaches said warning value.

18. The method of claim 14 that includes the further steps of measuring the value of said electrical output signal at predetermined time intervals to produce a plurality of value measurements, storing the value measurements, comparing one of said value measurements with another of said value measurements, and activating an alarm if the difference between the compared measured values exceeds a given level.

19. The method of claim 14, that further includes the step of providing a warning signal when the value of said electrical output signal is less than zero.

20. The method of claim 14, that further includes the steps of actuating a first light indicator when the value of the electrical output signal is within a first range of values; actuating a second light indicator when the value of the electrical output signal is within a second range of values; and actuating a third light indicator when the value of the electrical output signal is within a third range of values.

* * * * *